US00PP25618P2

(12) United States Plant Patent
Bae

(10) Patent No.: US PP25,618 P2
(45) Date of Patent: Jun. 16, 2015

(54) ***ACHILLEA* PLANT NAMED 'BALVINRED'**

(50) Latin Name: *Achillea millefolium*
Varietal Denomination: Balvinred

(71) Applicant: Ball Horticultural Company, West Chicago, IL (US)

(72) Inventor: JinJoo Bae, Sugar Grove, IL (US)

(73) Assignee: Ball Horticultural Company, West Chicago, IL (US)

( * ) Notice: Subject to any disclaimer, the term of this patent is extended or adjusted under 35 U.S.C. 154(b) by 133 days.

(21) Appl. No.: 13/987,959

(22) Filed: Sep. 18, 2013

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — Audrey Charles

(57) ABSTRACT

A new and distinct cultivar of *Achillea* plant named 'Balvinred', characterized by its medium red-colored inflorescences, medium green-colored foliage, and moderately vigorous, compact-upright growth habit, is disclosed.

1 Drawing Sheet

Latin name of genus and species of plant claimed: *Achillea millefolium.*
Variety denomination: 'Balvinred'.

BACKGROUND OF THE INVENTION

The present invention relates to a new and distinct cultivar of *Achillea* plant botanically known as *Achillea millefolium* and hereinafter referred to by the cultivar name 'Balvinred'.

The new cultivar originated in a controlled breeding program in Elburn, Ill. during June 2010. The objective of the breeding program was the development of *Achillea* cultivars having attractive flower coloration and a growth habit suitable for container plantings.

The new *Achillea* cultivar is the result of cross-pollination. The female (seed) parent of the new cultivar is the proprietary *Achillea millefolium* breeding selection coded 113-1, not patented, characterized by its light pink-colored inflorescences, medium green-colored foliage, and moderately vigorous, compact-upright growth habit. The male (pollen) parent of the new cultivar is the proprietary *Achillea millefolium* breeding selection coded 114-15, not patented, characterized by its medium red-colored inflorescences, medium green-colored foliage, and moderately vigorous, upright growth habit. The new cultivar was discovered and selected as a single flowering plant within the progeny of the above stated cross-pollination during July 2011 in a controlled environment in Elburn, Ill.

Asexual reproduction of the new cultivar by terminal stem cuttings since July 2011 in Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balvinred' as a new and distinct cultivar of *Achillea* plant:

1. Medium red-colored inflorescences;
2. Medium green-colored foliage; and
3. Moderately vigorous, compact-upright growth habit.

Plants of the new cultivar differ from plants of the female parent primarily in inflorescence color. Plants of the new cultivar differ from plants of the male parent primarily in having a more compact growth habit.

Of the many commercially available *Achillea* cultivars, the most similar in comparison to the new cultivar is 'Strawberry Seduction', U.S. Plant Pat. No. 18,401. However, in side by side comparisons, plants of the new cultivar differ from plants of 'Strawberry Seduction' in at least the following characteristics:

1. Plants of the new cultivar have a ray floret color different from plants of 'Strawberry Seduction'; and
2. Plants of the new cultivar are more compact than, as measured by plant height and width, than plants of 'Strawberry Seduction'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balvinred'. The plants were grown in the field for 10 weeks outdoors in West Chicago, Ill. Plants were given one pinch prior to transplant.

DETAILED BOTANICAL DESCRIPTION

Figure 1:
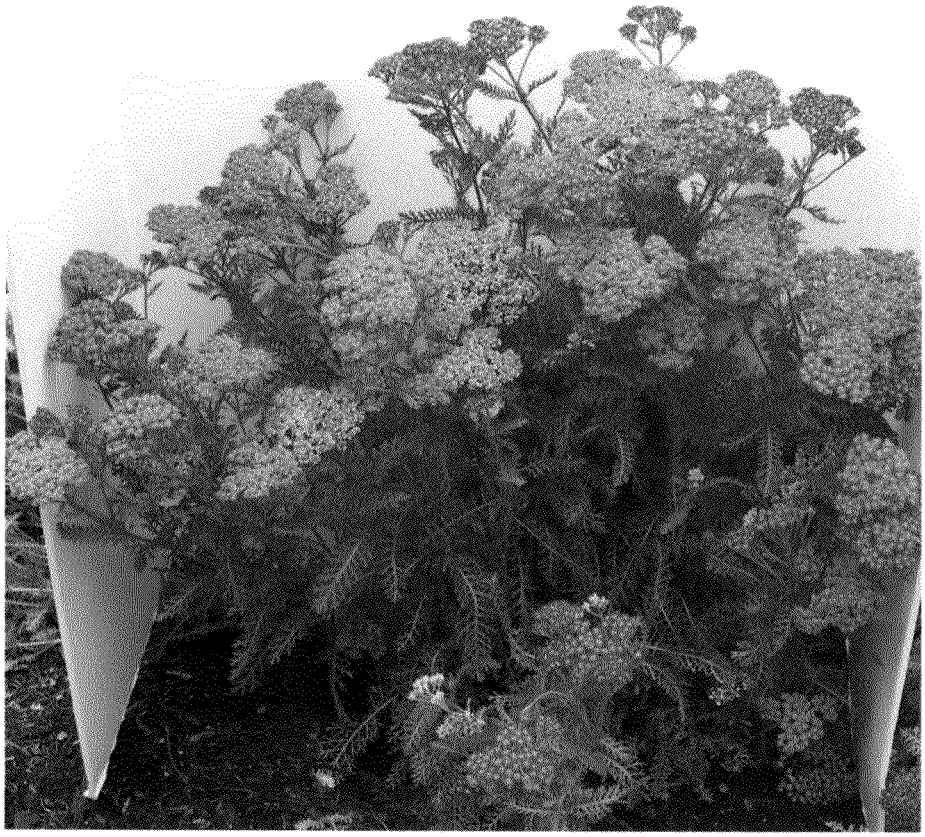
FIG. 1 illustrates a side view of the overall growth and flowering habit of 'Balvinred'.
Figure 2:
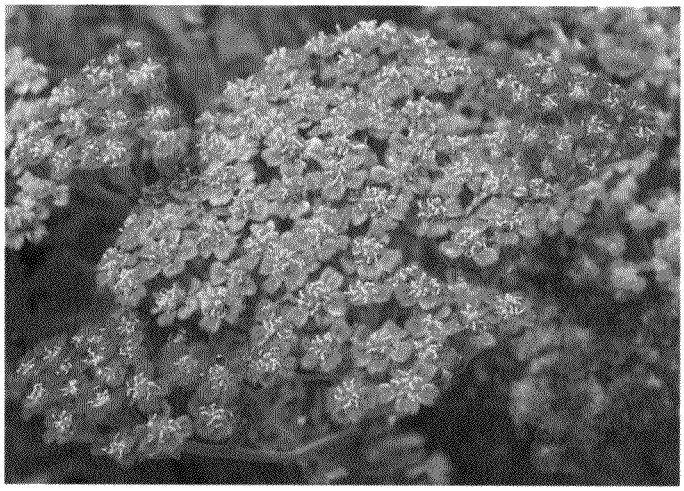
FIG. 2 illustrates a close-up view of an individual inflorescence of 'Balvinred'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2013 under natural light conditions in West Chicago, Ill.

The following descriptions and measurements describe plants produced from cuttings from stock plants and grown in a glass-covered greenhouse under conditions comparable to those used in commercial practice. After transplant, the plants were grown in 1.5 gallon containers for 10 weeks outdoors in West Chicago, Ill. utilizing a soilless growth medium. Plants were given one pinch prior to transplant. Greenhouse temperatures were maintained at approximately 50° F. to 70° F. (10.0° C. to 21.1° C.) during the day and approximately 35° F. to 50° F. (1.7° C. to 10.0° C.) during the night. No supplemental lighting was provided. Measurements and numerical values represent averages of typical plants.

Botanical classification: *Achillea millefolium* cultivar Balvinred.

Parentage:

*Female parent*.—Proprietary *Achillea millefolium* breeding selection coded 113-1, not patented.

*Male parent*.—Proprietary *Achillea millefolium* breeding selection coded 114-15, not patented.

Propagation:

*Type cutting*.—Terminal stem.

*Time to initiate roots*.—Approximately 10 to 12 days.

*Time to produce a rooted cutting*.—Approximately 4 weeks.

*Root description*.—Thick fibrous, white to light brown in color.

*Rooting habit*.—Freely branching, moderately dense.

Plant description:

*Commercial crop time*.—Approximately 14 weeks from a rooted cutting to finish in a 10 cm pot.

*Growth habit and general appearance*.—Compact-upright.

*Size*.—Height from soil level to top of plant plane: Approximately 39.5 cm. Width: Approximately 33.5 cm.

*Branching habit*.—Freely branching, pinching enhances basal branching. Quantity of main branches per plant: Approximately 17.

*Branch*.—Strength: Strong. Length to base of cyme: Approximately 29.5 cm. Diameter: Approximately 3.0 mm. Length of central internode: Approximately 2.7 cm. Texture: Tomentose. Color of young and mature stems: 146B.

Foliage description:

*General description*.—Quantity of leaves per main branch: Approximately 8. Fragrance: Faint. Form: Simple. Arrangement: Alternate.

*Leaves*.—Aspect: Acute angel to stem. Shape: Narrow oblanceolate. Margin: Very finely dissected giving a fern-like appearance. Apex: Acute. Base: Sessile, truncate. Venation pattern: Pinnate. Length of mature leaf: Approximately 8.2 cm. Width of mature leaf: 2.8 cm. Texture of upper and lower surfaces: Sparsely pubescent. Color of upper surface of young and mature foliage: 137B with midvein of 147C. Color of lower surface of young and mature foliage: 138A with midvein of 147C.

Flowering description:

*Flowering habit*.—'Balvinred' is freely flowering under outdoor growing conditions with substantially continuous blooming from late spring through summer.

*Lastingness of individual inflorescence on the plant*.—Approximately 10 to 14 days.

Inflorescence description:

*General description*.—Type: Rotate composite inflorescence form; inflorescences arranged in terminal or axillary compound cymes; cymes somewhat flat-topped; freely flowering; persistent. Aspect: Upward and outward. Quantity per plant: Approximately 17. Cyme diameter: Approximately 8.8 cm. Cyme depth: Approximately 4.8 cm. Inflorescence diameter: Approximately 6.0 mm. Inflorescence depth: Approximately 5.0 mm. Fragrance: Slight.

*Peduncle*.—Strength: Strong. Aspect: Erect. Length: Approximately 3.0 cm. Diameter: Approximately 2.0 mm. Texture: Tomentose. Color: 146B.

*Bud*.—Rate of opening: Generally takes 3 to 4 days for bud to progress from first color to fully open flower.

*Bud just before opening*.—Shape: Ovoid. Diameter: Approximately 3.0 mm. Color: 146D and petals of 71A.

*Ray florets*.—Quantity per inflorescence: Approximately 5. Arrangement: In a single whorl. Aspect: Rotate. Shape: Orbicular on a narrow tube enclosing pistil. Margin: Entire. Apex: Emarginate. Base: Attenuate. Length: Blade portion approximately 2.0 mm, tube portion approximately 3.0 mm. Width: Blade portion approximately 3.0 mm, tube portion approximately 0.5 mm. Texture of upper and lower surfaces: Glabrous. Color of upper surface when first open: 45A. Color of lower surface when first and fully open: 155D. Color of upper surface when fully open: 57C transitioning to N79C with senescence. Color of tube portion: 145B.

*Disc florets*.—Quantity per inflorescence: Approximately 15. Arrangement: Massed in center of inflorescence. Shape: Tubular. Margin: Entire. Apex: Five-acute tips. Base: Fused. Length: Approximately 4.0 mm. Diameter at apex: Approximately 1.0 mm. Diameter at base: Approximately 1.0 mm. Texture: Glabrous. Color when first and fully open: tips of 53B, center of 145B, and base of 145D.

*Disc*.—Diameter: Approximately 3.0 mm. Depth: Approximately 1.0 mm.

*Receptacle*.—Shape: Conical. Height: Approximately 1.0 mm. Diameter at base: Approximately 2.0 mm. Color: 144A.

*Phyllaries*.—Quantity per inflorescence Approximately 12. Arrangement: In multiple whorls. Shape: Lanceolate to narrowly elliptic. Margin: Entire with papery edges. Apex: Acute. Base: Truncate. Length: Approximately 2.0 to 4.0 mm. Width: Approximately 1.5 to 2.0 mm. Texture of upper surface: Glabrous. Texture of lower surface: Sparsely pubescent. Color of upper surface: 146B. Color of lower surface: 146D.

*Reproductive organs*.—Androecium: Present on disc florets only. Stamen quantity: 5. Stamen length: Approximately 2.0 mm. Anther shape: Oblong. Anther length: Approximately 1.0 mm. Anther color: 9A. Pollen amount: Abundant. Pollen color: 9B. Gynoecium: Present on ray and disc florets. Pistil quantity: 1 per floret. Pistil length: Approximately 4.0 mm. Stigma shape: Bifid. Stigma length: Less than 1.0 mm. Stigma color: NN155D, translucent. Style length: Approximately 3.0 mm. Style color: Lighter than 145D, translucent. Ovary length: Approximately 1.0 mm. Ovary color: 145D.

Seed and fruit production: Neither seed nor fruit production has been observed.

Disease and pest resistance: Resistance to pathogens and pests common to *Achillea* has not been observed.

What is claimed is:

1. A new and distinct cultivar of *Achillea* plant named 'Balvinred', substantially as herein illustrated and described.

* * * * *